United States Patent
Tsujino et al.

(10) Patent No.: US 6,740,129 B2
(45) Date of Patent: May 25, 2004

(54) ONE-PACK TYPE POST-FOAMABLE OXIDATION HAIR-DYE COMPOSITIONS

(75) Inventors: Yoshio Tsujino, Osaka (JP); Masahiro Aoki, Osaka (JP)

(73) Assignee: Henkel Lion Cosmetics Co. Ltd., Osaka (JP)

( * ) Notice: Subject to any disclaimer, the term of this patent is extended or adjusted under 35 U.S.C. 154(b) by 0 days.

(21) Appl. No.: 10/171,712

(22) Filed: Jun. 13, 2002

(65) Prior Publication Data

US 2003/0084517 A1 May 8, 2003

Related U.S. Application Data

(63) Continuation of application No. PCT/JP99/07273, filed on Dec. 24, 1999.

(51) Int. Cl.⁷ .................................................. A61K 7/13
(52) U.S. Cl. ..................... 8/405; 8/406; 8/409; 8/416
(58) Field of Search ........................... 8/405, 406, 409, 8/416

(56) References Cited

U.S. PATENT DOCUMENTS

| | | | |
|---|---|---|---|
| 4,961,925 A | * 10/1990 | Tsujino et al. | ............. 424/71 |
| 5,833,969 A | 11/1998 | Tsujino et al. | |
| 6,027,719 A | 2/2000 | Tomura et al. | |
| 6,228,129 B1 | 5/2001 | De La Mettrie et al. | |
| 6,241,784 B1 | 6/2001 | De La Mettrie et al. | |
| 6,251,145 B1 | 6/2001 | De La Mettrie et al. | |
| 6,254,646 B1 | 7/2001 | Di La Mettrie et al. | |
| 6,261,325 B1 | 7/2001 | De La Mettrie et al. | |
| 6,270,534 B1 | 8/2001 | De La Mettrie et al. | |
| 6,273,920 B1 | 8/2001 | De La Mettrie et al. | |
| 6,312,477 B1 | 11/2001 | De La Mettrie et al. | |
| 6,312,479 B1 | 11/2001 | Maubru | |
| 2002/0002747 A1 | 1/2002 | De La Mettrie et al. | |
| 2002/0010966 A1 | 1/2002 | De La Mettrie et al. | |
| 2002/0010967 A1 | 1/2002 | De La Mettrie et al. | |
| 2002/0013971 A1 | 2/2002 | Maubru | |

FOREIGN PATENT DOCUMENTS

| | | | |
|---|---|---|---|
| CA | 2150596 | 6/1996 | |
| EP | 0 310 675 | 1/1994 | |
| EP | 0 716 846 | 6/1996 | |
| EP | 0 875 241 | 11/1998 | |
| JP | 63-246313 | 10/1988 | |
| JP | 06-93126 | 4/1994 | |
| JP | 07-163861 | 6/1995 | |
| JP | 08-217652 | 8/1996 | |
| JP | 09-77629 | 3/1997 | |
| JP | 09-77630 | 3/1997 | |
| JP | 09077629 | * 3/1997 | ............ A61K/7/00 |
| JP | 10-298027 | 11/1998 | |
| JP | 10-316532 | 12/1998 | |
| JP | 11-12153 | 1/1999 | |
| WO | WO98/55083 | 12/1998 | |
| WO | WO 99/15137 | 4/1999 | |
| WO | WO99/17720 | 4/1999 | |
| WO | WO/9917721 | 4/1999 | |
| WO | WO99/17722 | 4/1999 | |
| WO | WO99/17723 | 4/1999 | |
| WO | WO99/17724 | 4/1999 | |
| WO | WO99/17725 | 4/1999 | |
| WO | WO99/17726 | 4/1999 | |
| WO | WO99/17727 | 4/1999 | |
| WO | WO99/17728 | 4/1999 | |
| WO | WO99/17729 | 4/1999 | |
| WO | WO99/17730 | 4/1999 | |
| WO | WO99/17731 | 4/1999 | |
| WO | WO99/17732 | 4/1999 | |
| WO | WO99/17733 | 4/1999 | |

OTHER PUBLICATIONS

Derwent WPI database, Accession No. 1997–241614 [22], abstract of JP 09 077629 (1997).
Derwent WPI database, Accession No. 1997–241615 [22], abstract of JP 09 077630 (1997).
Derwent WPI database, Accession No. 1999–407681 [35], abstract of JP 10 316532 (1999).

* cited by examiner

*Primary Examiner*—Brian P Mrux
*Assistant Examiner*—Eisa Elhilo
(74) *Attorney, Agent, or Firm*—Stephen D. Marper; Gregory M. Hill

(57) ABSTRACT

A one-package post-foaming oxidation hair dye composition containing uricase, uric acid, at least one oxidation dye, and at least one post-foaming agent is provided. The oxidation hair dye composition is packaged in a single package, and foams after spreading on hair.

13 Claims, No Drawings

ONE-PACK TYPE POST-FOAMABLE OXIDATION HAIR-DYE COMPOSITIONS

CROSS-REFERENCE TO RELATED APPLICATIONS

This application is a continuation under 35 U.S.C. §365 (c) and 35 U.S.C. §120 of international application PCT/JP99/07273, filed on Dec. 24, 1999, the international application not being published in English.

BACKGROUND OF THE INVENTION

The present invention relates to a one-package oxidation hair dye composition using uricase. More particularly, the present invention relates to a one-package post-foaming oxidation hair dye composition which is better in the use feeling and the handling property and which has the excellent dyeing effects to hair.

In previous oxidation hair dyes, color development was performed by mixing a first solution containing an oxidation dye and a second solution containing an oxidizing agent immediately before use, and oxidation-polymerizing the oxidation dye. However, since the oxidizing agent greatly damages hair due to its strong oxidizing force, in order to solve such the problems, the present inventors paid attention to the mild oxidizing action of enzymes and proposed a hair dye composition which contains a dielectron transfer oxidase as an acceptor and its donor as a substrate, and utilized the oxidation of an oxidation dye by the enzymatic oxidation reaction for hair dyeing (JP-A 63-246313). When this invention is used, since an oxidation reaction occurs first by the contact of the composition with oxygen, a one-package oxidation hair dye was obtainable by blocking oxygen from the composition.

Thereafter, we studied extensively, as a result, a hair dye composition having improved stability with uricase, and more practicability was obtained by selecting a combination of certain ingredients regarding uricase in the hair dye composition of JP-A 63-246313 (JP-A 8-217652).

However, a one-package oxidation hair dye using uricase has a problem that uric acid, which is a substrate for uricase, is difficult to dissolve. In order to solve this problem, the present inventors proposed the technology of solubilizing uric acid (JP-A 10-298027). Since when this invention is used, uric acid can be solubilized instead of being dispersed, resulting in more excellent hair dyeing properties relative to before, even when the dye concentration was lowered.

However, there was a problem that in the one-package oxidation hair dye using such solubilizing techniques, the amount of generated hydrogen peroxide was small compared with the previous two-package oxidation hair dye. This resulted in the dyeing properties being weak, even though damage to the hair was alleviated.

The present inventors studied extensively and found that the hair dyeing properties not satisfied can be improved by incorporating a post-foaming agent. Although there are a number of applications relating to post-foaming compositions (see JP-A 6-93126, JP-A 7-163861, JP-A9-077629, JP-A 9-077630 and JP-A 10-316532), since an oxidation hair dye is usually in a two-package form, mixing is necessary immediately before use, and it is difficult to obtain the post-foaming property. A one-package oxidation hair dye can first give the post-foaming property.

SUMMARY OF THE INVENTION

Accordingly, the present invention provides a one-package post-foaming oxidation hair dye composition that contains uricase, uric acid, an oxidation dye, and a post-foaming agent.

The characteristics of the post-foaming property are as follows: A post foaming composition is gel-like immediately after it is applied onto the hair, but foams on the whole hair after spreading, such as with a brush or the like. The areas of hair containing the oxidation hair dye are then easily recognized, and the oxidation hair dye has excellent feel and handling properties. For example, the oxidation hair dye does not run off the hair.

DETAILED DESCRIPTION OF THE INVENTION

Uricase contained in the one-package post-foaming oxidation hair dye composition of the present invention is an oxidase, also called uric acid oxidase, and is a dielectron transfer oxidase contained in the liver, kidney, spleen and the like of mammals, but not primates. The concentration of uricase to be contained in the hair dye composition is in a range of 100 to 50,000 I.U./100 g, preferably 1,000 to 30,000 I.U./100 g. When the content is less than 100 I.U./100 g, a sufficient hair dyeing effect cannot be obtained. On the other hand, even when the uricase concentration exceeds 50,000 I.U./100 g, the hair dyeing effect is not further increased. Accordingly, it is not advantageous in view of the costs to exceed 50,000 I.U./100 g. As used herein, the unit for enzyme activity "I.U." represents an international unit and corresponds to an amount of the enzyme activity which converts 1 $\mu$mol uric acid into a product for 1 minute under the conditions of 25° C. and pH 8.5.

Uric acid, which is a substrate for uricase, is also an essential ingredient in the one-package post-foaming oxidation hair dye composition of the present invention. In the oxidation hair dye composition of the present invention, an oxidation dye is polymerized in hair to produce a pigment and dye hair by an enzymatic oxidation reaction. The enzymatic oxidation reaction involves reacting uricase with uric acid, where the uric acid is a substrate as a donor under suitable use conditions. As used herein, "uric acid" includes its salt. The content of the uric acid in the oxidation hair dye composition is preferably 0.1 to 5.0% by weight. When the content of uric acid, which is a donor, is less than the above range, a sufficient dyeing effect cannot be obtained, and when the content is greater than the above range, the dyeing effect is not further increased as in the case of the enzyme.

Further, in the one-package post-foaming oxidation hair dye composition of the present invention, a post-foaming agent is also an essential ingredient. The post-foaming agent used in the present invention has a boiling point of not higher than 40° C. Examples of post foaming agents include aliphatic hydrocarbons such as propane, i-butane, n-butane, pentane, isopentane and the like, dimethyl ether and divinyl ether. The content of the post-foaming agent in the oxidation hair dye composition is suitably 0.1 to 10.0% by weight, preferably, 0.5 to 3.0% by weight. When the content of the post-foaming agent is less than 0.1% by weight, a sufficient post-foaming property cannot be obtained in some cases. Conversely, when the content exceeds 10.0% by weight, foaming occurs immediately, and a better post-foaming property cannot be obtained in some cases.

In the one-package post-foaming oxidation hair dye composition of the present invention, its pH is adjusted to 7.5 to 9.5. Examples of pH adjusting agents which can be used in the present invention are basic amine agents such as monoethanolamine (MEA), diethanolamine (DEA), triethanolamine (TEA), 2-amino-2-methyl-1-propanol (AMP), 2-amino-2-methyl-1,3-propanediol (AMPD), monoisopropanolamine (MIPA), and tetrakis(2-hydroxyisopropyl) ethylenediamine (TE). These basic agents can be used alone or in combination with each other. Inorganic alkali agents, such as ammonia, sodium hydroxide, potassium hydroxide and the like can also be used.

In the present composition, the kind and amount of the oxidation dye are not particularly limited and can be selected from known ones. For example, the following oxidation dyes may be used in an appropriate amount: 5-aminoorthocresol, 3,3'-iminodiphenol, 2,4-diaminophenol hydrochloride, 2,5-diaminotoluene hydrochloride, paraphenylenediamine hydrochloride, N-phenylparaphenylenediamine hydrochloride, metaphenylenediamine hydrochloride, ortho-aminophenol, catechol, N-phenylparaphenylenediamine acetate, 2,6-diaminopyridine, 1,5-dihydroxynaphthalene, diphenylamine, toluene-2,5-diamine, toluene-3,4-diamine, α-naphthol, paraaminophenol, paraphenylene-diamine, paramethylaminophenol, hydroquinone, pyrogallol, N-phenylpara-phenylenediamine, phloroglucin, metaaminophenol, metaphenylenediamine, 5-aminoorthocresol sulfate, orthoaminophenol sulfate, orthochloropara-phenylenediamine sulfate, 4,4'-diaminodiphenylamine sulfate, 2,4-diaminophenol sulfate, 2,5-diaminotoluene sulfate, paraaminophenol sulfate, paraphenylene-diamine sulfate, paramethylaminophenol sulfate, metaaminophenol sulfate, metaphenylenediamine sulfate, 2,4-diaminophenoxyethanol hydrochloride, or 5-(2-hydroxyethylamino)-2-methylphenol described in Japanese Standards of Quasi-drug Ingredients (published by THE YAKUJI NIPPO LIMITED, edited by Society of Japanese Pharmacopoeia, supervised by Pharmaceuticals and Cosmetics Division, Pharmaceutical Affairs Bureau, Ministry of Health and Welfare on June, 1991). Further, 2,2'-[(4-aminophenyl)imino]bisethanol can also be used in an appropriate amount.

In addition, direct dyes such as 2-amino-4-nitrophenol, 2-amino-5-nitrophenol, 1-amino-4-methylamino-anthraquinone, nitroparaphenylenediamine hydrochloride, 1,4-diaminoanthraquinone, nitroparaphenylenediamine, picramic acid, sodium picramate, 2-amino-5-nitrophenol sulfate, resorcinol, nitroparaphenylenediamine sulfate, paranitroorthophenyleneediamine sulfate, paranitrometaphenylenediamine sulfate and the like which are usually used together with an oxidation dye can be included in the composition of the invention. Preferable oxidation dyes used in the present composition are paraphenylenediamine and its salt, paraaminophenol, orthoaminophenol, metaaminophenol, paranitroortho- phenylenediamine, 2,6-diaminopyridine, resorcinol, orthoaminophenol, and metaphenylenediamine hydrochloride. These dyes can be used alone or in combination thereof.

The one-package post-foaming oxidation hair dye composition of the present invention can be applied to previous oxidation hair dyes using a dielectron transfer oxidase and a substrate and further including a post-foaming agent. Examples of such oxidation hair dyes are oxidation hair dyes described in WO98/55083, WO99/17720, WO99/17721, WO99/17722, WO99/17723, WO99/17724, WO99/17725, WO99/17726, WO99/17727, WO99/17728, WO99/17729, WO99/17730, WO99/17731, WO99/17732, WO99/17733, JP-A 63-246313, JP-A 8-217652, JP-A 10-298027, and JP-A 11-012153.

EXAMPLES

The one-package post-foaming oxidation hair dye composition of the present invention will be explained by way of the Test Example, Examples, and Comparative Example.

Test Example

Using the following ingredients and isopentane as a post-foaming agent as shown in Table 1, and varying the amounts of isopentane, one-package post-foaming oxidation hair dye compositions were prepared. In addition, as a control composition, an oxidation hair dye composition containing the same ingredients except that isopentane was not incorporated therein was prepared.

TABLE 1

| Ingredient | Test Ex. 1 | Test Ex. 2 | Test Ex. 3 | Test Ex. 4 | Test Ex. 5 | Control |
|---|---|---|---|---|---|---|
| Paraphenylenediamine | 0.60 | 0.60 | 0.60 | 0.60 | 0.60 | 0.60 |
| Paramethylaminophenol sulfate | 0.30 | 0.30 | 0.30 | 0.30 | 0.30 | 0.30 |
| 2,4-Diaminophenoxyethanol hydrochloride | 0.05 | 0.05 | 0.05 | 0.05 | 0.05 | 0.05 |
| Paraaminophenol | 0.10 | 0.10 | 0.10 | 0.10 | 0.10 | 0.10 |
| 5-Aminoorthocresol | 0.05 | 0.05 | 0.05 | 0.05 | 0.05 | 0.05 |
| Resorcinol | 0.50 | 0.50 | 0.50 | 0.50 | 0.50 | 0.50 |
| N-acetylL-cysteine | 0.08 | 0.08 | 0.08 | 0.08 | 0.08 | 0.08 |
| Alkyl acrylate-alkyl methacrylate-polyoxyethylene ester copolymer emulsion (30%) | 2.50 | 2.50 | 2.50 | 2.50 | 2.50 | 2.50 |
| Sorbitol | 3.00 | 3.00 | 3.00 | 3.00 | 3.00 | 3.00 |
| Polyoxyethylenemethyl-glucoside | 1.00 | 1.00 | 1.00 | 1.00 | 1.00 | 1.00 |
| Polypeptide coconut oil fatty acid potassium | 1.00 | 1.00 | 1.00 | 1.00 | 1.00 | 1.00 |
| Monoethanolamine | | | to pH of 9.2 | | | |
| Uric acid | 1.00 | 1.00 | 1.00 | 1.00 | 1.00 | 1.00 |
| Uricase (20 I.U./mg) | 1.00 | 1.00 | 1.00 | 1.00 | 1.00 | 1.00 |
| Isopentane | 0.50 | 1.00 | 1.50 | 2.00 | 3.00 | 0.00 |
| Purified water | | | Balance | | | |

Hair dyeing tests were performed using the one-package post-forming oxidation hair dye compositions of Test Examples 1 to 5 and a control composition. The test procedure was as follows: The composition was contacted with a goat hair bundle at a ratio of goat hair bundle to composition of 1:2 by volume. The hair bundle was dyed at 30° C. for 30 minutes, washed with water, dried and observed. The dyeing effect on the treated goat bundle was evaluated with naked eyes according to the following criteria. These results are shown in Table 2.

●: Densely dyed

○: Dyed (corresponding to dyeability of Comparative Example)

Δ: Less densely dyed

×: Hardly dyed

TABLE 2

| | Test Ex. 1 | Test Ex. 2 | Test Ex. 3 | Test Ex. 4 | Test Ex. 5 | Comp. Ex. |
|---|---|---|---|---|---|---|
| Dyeing effect | ● | ● | ● | ● | ● | ○ |

As apparent from Table 2, it was shown that, in the one-package post-foaming oxidation hair dye composition of the present invention, the post-foaming formulation can improve the dyeing effect.

Example 1

According to the following formulation, a hair dye composition of the present invention was prepared by a conventional method.

| Ingredient | Amount (% by weight) |
|---|---|
| Paraphenylenediamine | 0.5 |
| 2,4-Diaminophenoxyethanol hydrochloride | 0.05 |
| 2-[[4-(dimethylamino)phenyl]azo]-1,3-dimethyl-imidazolium chloride | 0.1 |
| (1-Methyl-1-phenyl)-2-(1-methine-4N-methylpyridinium) hydrazine chloride | 0.05 |
| 4-Aminophenylazo-2N-methyl-5N-methylimidazolium chloride | 0.05 |
| L-cysteine | 0.2 |
| Alkyl acrylate-alkyl methacrylate polyoxyethylene ester copolymer emulsion (30%) | 3.5 |
| Decaglyceryl monomyristate | 1.0 |
| Monoisopropanolamine | to pH 9.0 |
| Uric Acid | 1.0 |
| Uricase (20 I.U./mg) | 1.0 |
| Isopentane | 2.0 |
| Purified Water | Balance |
| Total | 100 |

Example 2

According to the following formulation, a hair dye composition of the present invention was prepared by a conventional method.

| Ingredient | Amount (% by weight) |
|---|---|
| Paraphenylenediamine | 0.6 |
| Methaphenylenediamine hydrochloride | 0.1 |
| Thioglycolic acid | 0.2 |
| Xanthan gum | 2.0 |
| Polyoxyethylene (4.2) lauryl ether | 3.0 |
| Potassium hydroxide | to pH 9.0 |
| Uric Acid | 1.0 |
| Uricase (20 I.U./mg) | 1.0 |
| Isopentane | 2.0 |
| Purified Water | Balance |
| Total | 100 |

Example 3

According to the following formulation, a hair dye composition of the present invention was prepared by a conventional method.

| Ingredient | Amount (% by weight) |
|---|---|
| Paraphenylenediamine | 0.3 |
| 2-Amino-3-hydroxypyridine | 0.3 |
| N-Acetyl-L-cysteine | 0.2 |
| Ethanol | 20.0 |
| Hydroxyethyl cellulose | 2.0 |
| Alkyl (8 to 10) glucoside | 5.0 |
| Monoethanolamine | to pH 9.0 |
| Uric Acid | 1.0 |
| Uricase (20 I.U./mg) | 1.0 |
| Isopentane | 2.0 |
| Purified Water | Balance |
| Total | 100 |

Example 4

According to the following formulation, a hair dye composition of the present invention was prepared by a conventional method.

| Ingredient | Amount (% by weight) |
|---|---|
| Paraphenylenediamine | 0.5 |
| 1,3-Dihydroxybenzene | 0.3 |
| N-Acetyl-L-cysteine | 0.2 |
| Propylene glycol monomethyl ether | 20.0 |
| Hydroxyethyl cellulose | 2.0 |
| Alkyl (8 to 10) glucoside | 5.0 |
| Monoethanolamine | to pH 9.0 |
| Uric Acid | 1.0 |
| Uricase (20 I.U./mg) | 1.0 |
| Isopentane | 2.0 |
| Purified Water | Balance |
| Total | 100 |

Industrial Applicability

As explained above, in the one-package post-foaming oxidation hair dye composition of the present invention, the post-foaming formulation provides a one-package post-foaming hair dye composition which can improve the hair dyeing effect and which is excellent in the use feeling and the handling property. This one-package post-foaming oxidation hair dye composition is useful for oxidation hair dyes utilizing a dielectron transfer oxidase and its substrate.

What is claimed is:

1. A one-package post-foaming oxidation hair dye composition, wherein the oxidation hair dye composition comprises:
   a) uricase,
   b) uric acid,
   c) at least one oxidation dye, and
   d) at least one post-foaming agent comprising at least one organic solvent having a boiling point of not higher than 40° C.; and
   wherein the oxidation hair dye composition is packaged in a single package and foams after spreading on hair.

2. The composition of claim 1, wherein the oxidation hair dye composition is in a form of a gel for application to hair and foams after spreading on the hair.

3. The composition of claim 2, wherein the post-foaming agent comprises from 0.1 weight percent to 10 weight percent, based on the total weight of the oxidation hair dye composition.

4. The composition of claim 1, wherein the organic solvent comprises propane, isobutane, n-butane, pentane, isopentane or dimethyl ether, or combinations thereof.

5. The composition of claim 2, wherein the oxidation dye is present in the oxidation hair dye composition in an amount of from 0.1 weight percent to 5.0 weight percent, based on the total weight of the oxidation hair dye composition.

6. The composition of claim 5, wherein the uric acid is present in the oxidation hair dye composition in an amount of from 0.1 weight percent to 5.0 weight percent, based on the total weight of the oxidation hair dye composition.

7. The composition of claim 6, wherein the uricase is present in the oxidation hair dye composition in an amount of from 1000 I.U./100 g to 30000 I.U./100 g, based on the total weight of the oxidation hair dye composition.

8. The composition of claim 2, wherein the uric acid is present in the oxidation hair dye composition in an amount of from 0.1 weight percent to 5.0 weight percent, based on the total weight of the oxidation hair dye composition.

9. The composition of claim 2, wherein the uricase is present in the oxidation hair dye composition in an amount of from 1000 I.U./100 g to 30000 I.U./100 g, based on the total weight of the oxidation hair dye composition.

10. The composition of claim 2, wherein the oxidation hair dye composition comprises at least one direct dye.

11. A method of dyeing hair comprising applying the oxidation hair dye composition of claim 1 to hair.

12. The method of claim 11, wherein the oxidation hair dye composition is applied to the hair as a gel.

13. The method of claim 12, wherein the post-foaming agent comprises from 0.1 weight percent to 10 weight percent, based on the total weight of the oxidation hair dye composition, of at least one organic solvent having a boiling point of not higher than 40° C.

* * * * *